US00PP27388P2

(12) United States Plant Patent
Kitahara

(10) Patent No.: US PP27,388 P2
(45) Date of Patent: Nov. 15, 2016

(54) ***VERBENA* PLANT NAMED 'AKIV28902M'**

(50) Latin Name: *Verbena hybrida*
Varietal Denomination: AKIV28902M

(71) Applicant: Akiko Kitahara, Hikone Shiga (JP)

(72) Inventor: Akiko Kitahara, Hikone Shiga (JP)

(73) Assignee: Plant 21 LLC, Bonsall, CA (US)

( * ) Notice: Subject to any disclaimer, the term of this patent is extended or adjusted under 35 U.S.C. 154(b) by 172 days.

(21) Appl. No.: 14/121,730

(22) Filed: Oct. 11, 2014

(51) Int. Cl.
*A01H 5/02* (2006.01)

(52) U.S. Cl.
USPC ..... Plt./308

(58) Field of Classification Search
USPC ..... Plt./308
See application file for complete search history.

*Primary Examiner* — Keith Robinson
(74) *Attorney, Agent, or Firm* — C. A. Whealy

(57) ABSTRACT

A new and distinct cultivar of *Verbena* plant named 'AKIV28902M', characterized by its compact, outwardly spreading and mounding to trailing plant habit; vigorous growth habit; freely branching habit; freely flowering habit; and cherry red and white bi-colored flowers that are held above and beyond the foliar plane.

1 Drawing Sheet

Botanical designation: *Verbena hybrida.*
Cultivar denomination: 'AKIV28902M'.

BACKGROUND OF THE INVENTION

The present invention relates to a new and distinct cultivar of *Verbena* plant, botanically known as *Verbena hybrida*, and hereinafter referred to by the name 'AKIV28902M'.

The new *Verbena* plant is a naturally-occurring branch mutation of a proprietary seedling selection of *Verbena hybrida* identified as code number 07V289-02, not patented. The new *Verbena* plant was discovered and selected by the Inventor on a single flowering plant within a population of plants of the mutation parent in a controlled greenhouse environment in Gensingen, Germany on Sep. 14, 2011.

Asexual reproduction of the new *Verbena* plant by terminal cuttings in a controlled greenhouse environment in Gensingen, Germany since Sep. 15, 2011 has shown that the unique features of this new *Verbena* plant are stable and reproduced true to type in successive generations.

SUMMARY OF THE INVENTION

Plants of the new *Verbena* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'AKIV28902M'. These characteristics in combination distinguish 'AKIV28902M' as a new and distinct *Verbena* plant:

1. Compact, outwardly spreading and mounding to trailing plant habit.
2. Vigorous growth habit.
3. Freely branching habit.
4. Freely flowering habit.

5. Cherry red and white bi-colored flowers that are held above and beyond the foliar plane.

Plants of the new *Verbena* can be compared to plants of the mutation parent selection. Plants of the new *Verbena* differ primarily from plants of the mutation parent selection in flower color as plants of the mutation parent selection have solid cherry red-colored flowers.

Plants of the new *Verbena* can be compared to plants of the *Verbena hybrida* 'VEAZ0011', disclosed in U.S. Plant Pat. No. 24,006. In side-by-side comparisons conducted in Bonsall, Calif., plants of the new *Verbena* differed primarily from plants of 'VEAZ0011' in the following characteristics:

1. Leaves of plants of the new *Verbena* were lighter green in color than leaves of plants of 'VEAZ0011'.
2. Plants of the new *Verbena* and 'VEAZ0011' differed in flower color as plants of 'VEAZ0011' had scarlet red and white bi-colored flowers.

Plants of the new *Verbena* can also be compared to plants of the *Verbena hybrida* 'Lan Lay Star', disclosed in U.S. Plant Pat. No. 14,590. In side-by-side comparisons conducted in Bonsall, Calif., plants of the new *Verbena* differed primarily from plants of 'Lan Lay Star' in the following characteristics:

1. Plants of the new *Verbena* were more mounding than and not as creeping as plants of 'Lan Lay Star'.
2. Plants of the new *Verbena* and 'Lan Lay Star' differed in flower color as plants of 'Lan Lay Star' had lavender blue and white bi-colored flowers.

BRIEF DESCRIPTION OF THE PHOTOGRAPHS

The accompanying colored photographs illustrate the overall appearance of the new *Verbena* plant showing the colors as true as it is reasonably possible to obtain in colored reproductions of this type. Colors in the photographs may differ slightly from the color values cited in the detailed botanical description which accurately describe the actual colors of the new *Verbena* plant.

The photograph at the bottom of the sheet comprises a side perspective view of a typical flowering plant of 'AKIV28902M' grown in a container.

The photograph at the top of the sheet is a close-up view of a typical flowering plant of 'AKIV28902M'.

DETAILED BOTANICAL DESCRIPTION

The aforementioned photographs and following observations, measurements and values describe plants grown during the spring in 10-cm containers in a polyethylene-covered greenhouse and subsequently in an outdoor nursery in Bonsall, Calif. During the production of the plants, day temperatures ranged from 18° C. to 24° C. and night temperatures ranged from 13° C. to 16° C. Plants were pinched two times and were six weeks old when the photographs and description were taken. In the following description, color references are made to The Royal Horticultural Society Colour Chart, 2007 Edition, except where general terms of ordinary dictionary significance are used.

Botanical classification: *Verbena hybrida* 'AKIV28902M'.

Parentage: Naturally-occurring branch mutation of a proprietary seedling selection of *Verbena hybrida* identified as code number 07V289-02, not patented.

Propagation:

*Type cutting*.—Vegetative tip cuttings.

*Time to initiate roots, summer*.—About three days at temperatures ranging from about 16° C. to 29° C.

*Time to initiate roots, winter*.—About four days at temperatures ranging from about 16° C. to 21° C.

*Time to produce a rooted plant, summer*.—About 15 days at temperatures ranging from about 16° C. to 29° C.

*Time to produce a rooted plant, winter*.—About 20 days at temperatures ranging from about 16° C. to 21° C.

*Root description*.—Medium in thickness, fibrous.

*Rooting habit*.—Freely branching; medium density.

Plant description:

*Plant and growth habit*.—Compact, outwardly spreading and mounding to trailing plant habit; freely branching habit with about seven primary lateral branches developing per plant each with numerous secondary branches; pinching enhances lateral branch development; dense and bushy plant habit; vigorous growth habit.

*Plant height*.—About 11.5 cm.

*Plant diameter* (*spread*).—About 28 cm.

Lateral branch description:

*Length*.—About 17.5 cm.

*Diameter*.—About 2 mm.

*Internode length*.—About 2.5 cm.

*Orientation*.—Initially upright then outwardly spreading and decumbent.

*Strength*.—Strong.

*Texture*.—Pubescent.

*Color*.—Close to 146A.

Leaf description:

*Arrangement*.—Opposite, simple.

*Length*.—About 4 cm.

*Width*.—About 2.5 cm.

*Shape*.—Oblong to ovate.

*Apex*.—Broadly acute.

*Base*.—Attenuate.

*Margin*.—Broadly crenate.

*Texture, upper and lower surfaces*.—Pubescent; coarse, hirsute.

*Venation pattern*.—Pinnate; reticulate.

*Color*.—Developing leaves, upper surface: Close to 137B. Developing leaves, lower surface: Close to 144A. Fully expanded leaves, upper surface: Close to 147A; venation, close to 145A. Fully expanded leaves, lower surface: Close to 147B; venation, close to 147C.

*Petiole*.—Length: About 7 mm. Diameter: About 2.5 mm. Texture, upper and lower surfaces: Pubescent. Color, upper surface: Close to 145A. Color, lower surface: Close to 147C.

Flower description:

*Flower arrangement and habit*.—Sessile salverform flowers arranged in compact hemispherical terminal racemes; flowers face upward or outwardly; freely flowering habit with about 33 flowers developing per inflorescence and typically more than 450 flowers developing per plant.

*Natural flowering season*.—Plants flower continuously from spring through the autumn in southern California; early flowering habit, plants begin flowering about six weeks after planting.

*Flower longevity*.—Flowers last about five days on the plant; flowers not persistent.

*Fragrance*.—None detected.

*Inflorescence height*.—About 3.6 cm.

*Inflorescence diameter*.—About 5.8 cm.

*Flower buds*.—Length: About 1.8 cm. Diameter: About 3 mm. Shape: Elongated oblong. Color: Close to 69A.

*Flower diameter*.—About 1.6 cm.

*Flower depth* (*height*).—About 2.7 cm.

*Throat diameter*.—About 2 mm.

*Tube length*.—About 2.2 cm.

*Tube diameter, proximal*.—About 2.5 mm.

*Corolla*.—Arrangement: Single whorl of five fused petals fused towards the base into a narrow tube. Petal lobe length: About 8 mm. Petal lobe width: About 7 mm. Petal lobe shape: Roughly cordate. Petal lobe apex: Emarginate to cordate, slightly sinuate. Petal margin: Entire to emarginate. Petal texture, upper and lower surfaces: Smooth, glabrous; velvety. Throat texture: Smooth, glabrous. Tube texture: Sparsely pubescent. Color: Petal, when opening, upper surface: Close to 63B to 63C. Petal, when opening, lower surface: Close to 69A. Petal, fully opened, upper surface: Close to 53C to 53D and N155D; colors becoming closer to 64D and N155D with development. Petal, fully opened, lower surface: Close to 63D and N155C; color does not change with development. Throat: Close to 145B and 145C. Tube: Close to 145D.

*Calyx*.—Arrangement: Single whorl of five fused sepals fused towards the base into a slender tube. Sepal length: About 1.3 cm. Sepal width: About 1 mm. Sepal shape: Narrowly lanceolate. Sepal apex: Acute. Sepal margin: Entire. Sepal texture, inner surface: Smooth, glabrous. Sepal texture, outer surface: Pubescent; minute. Sepal color, upper surface: Close to 144A. Sepal color, lower surface: Close to 147B.

*Peduncles*.—Length: About 5.5 cm. Diameter: About 2 mm. Strength: Strong. Texture: Pubescent. Color: Close to 146A.

*Reproductive organs*.—Stamens: Quantity and arrangement: Four per flower, filaments are adnate to corolla tube. Filament length, free section: Less than 1 mm. Filament color: Close to 145C. Anther shape: Oval. Anther length: About 1 mm. Anther color: Close to N144A. Pollen amount: Scarce. Pollen color: Close to N144D. Pistils: Quantity: One per flower. Pistil length: About 2 cm. Stigma shape: Rounded, bi-parted. Stigma color: Close to 144A. Style length: About 1.8 cm. Style color: Close to 145D. Ovary color: Close to 144A. Fruits and seeds: Fruit and seed development have not been observed on plants of the new *Verbena*.

Temperature tolerance: Plants of the new *Verbena* have been observed to tolerate temperatures from about 1° C. to about 40° C.

Pathogen & pest resistance: Plants of the new *Verbena* have been observed to be relatively tolerant to powdery mildew. Plants of the new *Verbena* have not been observed to be resistant to pests and other pathogens common to *Verbena* plants.

It is claimed:

1. A new and distinct *Verbena* plant named 'AKIV28902M' as illustrated and described.

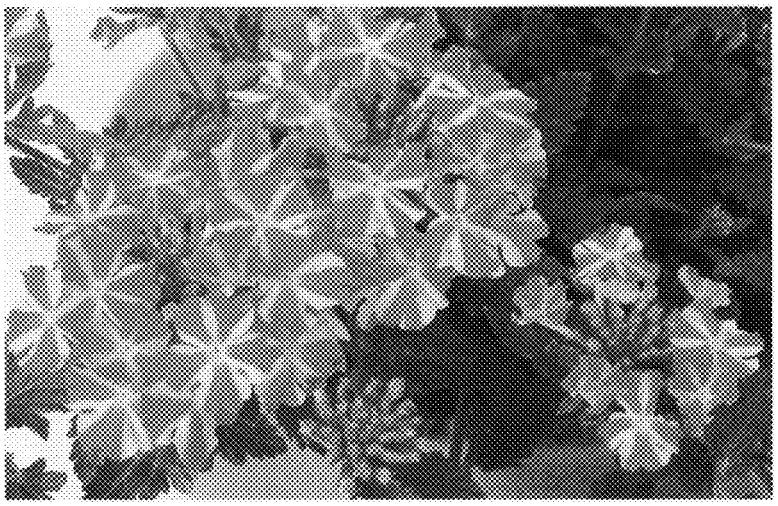
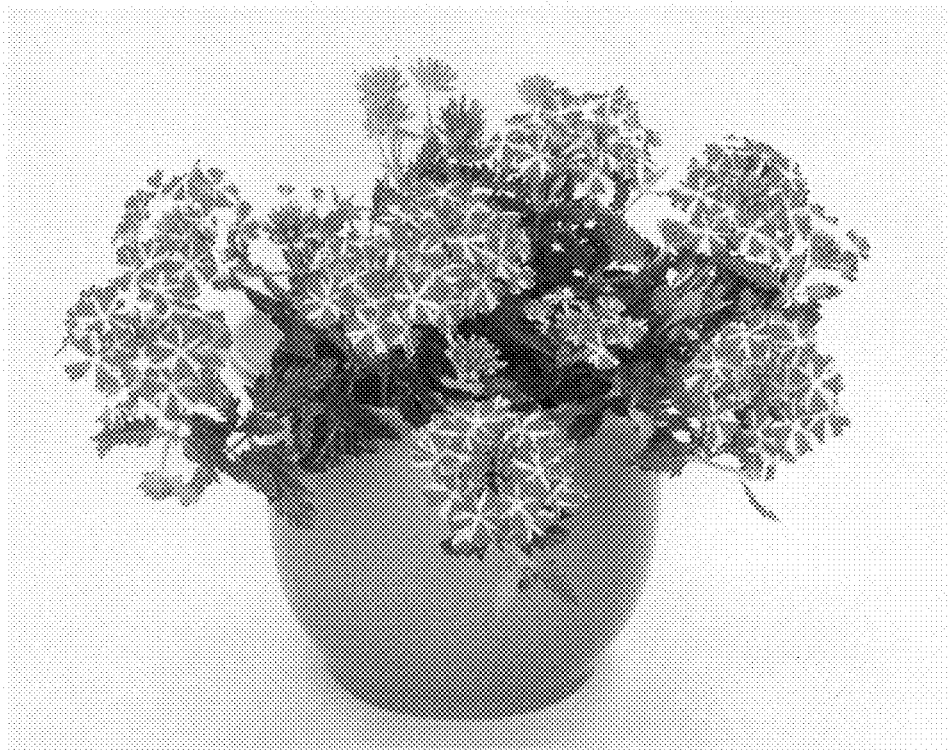

* * * * *